United States Patent [19]

Urella

[11] Patent Number: 4,552,164

[45] Date of Patent: Nov. 12, 1985

[54] DETECTION METHOD AND APPARATUS

[76] Inventor: Tony Urella, R.D. #2, Bernville, Pa. 19506

[21] Appl. No.: 288,747

[22] Filed: Jul. 31, 1981

[51] Int. Cl.[4] .............................................. A62B 7/02
[52] U.S. Cl. .................................... 137/2; 128/204.22
[58] Field of Search ................... 128/204.22; 250/343; 137/1, 2, 3, 551

[56] References Cited

U.S. PATENT DOCUMENTS

| 2,299,109 | 10/1942 | Rand | 128/204.22 |
| 3,593,735 | 7/1971 | Reicher | 128/204.22 X |
| 4,233,513 | 11/1980 | Elder | 250/343 |
| 4,326,807 | 4/1982 | Zochbauer | 250/343 X |

FOREIGN PATENT DOCUMENTS 1149767  4/1969  United Kingdom ........... 128/202.22

Primary Examiner—Alan Cohan
Attorney, Agent, or Firm—Huff & Hanson

[57] ABSTRACT

A method and apparatus as disclosed herein to detect the presence of anesthetic gas in the oxygen-containing gas delivery line, for use with a system for administration of anesthetics, which anesthetics comprise predominantly a mixture of an anesthetic gas, for example, nitrous oxide, and an oxygen-containing gas. A sensor is provided to develop a first signal when the presence of anesthetic gas is detected in the oxygen-containing gas delivery line. The first signal is used to generate an output signal which is transmitted to an audio and/or visual warning device or means which will shut off the incoming oxygen-containing gas stream.

12 Claims, 1 Drawing Figure

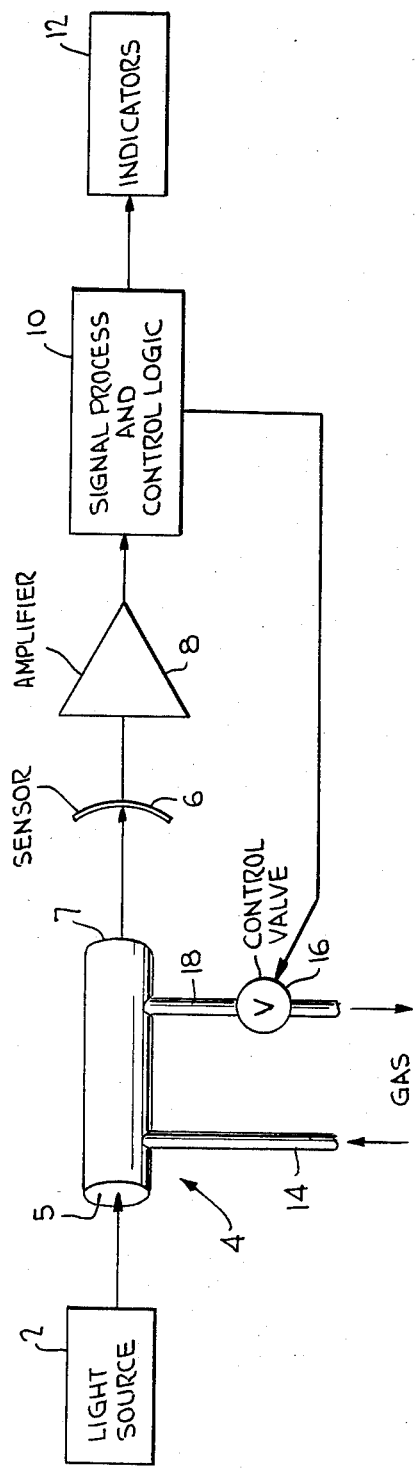

DETECTION METHOD AND APPARATUS

FIELD OF THE INVENTION

This invention relates to a method and an apparatus for detecting the presence of anesthetic gases in the oxygen-containing gas line used in the administration of anesthetic gases in a medical environment and is more particularly concerned with the detection of anesthetic gases, for example, nitrous oxide, in the oxygen-containing gas delivery line prior to mixing the anesthetic gas and the oxygen-containing gas for subsequent administration of the mixture of the gases to anesthetize a patient.

DESCRIPTION OF THE PRIOR ART

Generally, for the administration of anesthetic gases in a medical environment an anesthetic gas, for example, nitrous oxide, is mixed with oxygen or an oxygen-containing gas by an anesthetist or like trained personnel, utilizing flow meters or like regulatory or gas flow equipment at the site of the anesthetising procedure. This allows variance in the amount of anesthetizing gas which is being delivered to the patient.

Most major medical facilities utilize anesthetic gas and oxygen or oxygen-containing gas delivery lines directly into the operating room or like facility where anesthetic gases are administered to patients. In many instances the anesthetic gases and oxygen or oxygen-containing gases are conducted via delivery lines to the various areas in the medical facility from a centralized location which may be a significant distance from the location where the anesthetic is administered to the patient. In smaller medical or dental facilities the anesthetic gas and oxygen or oxygen-containing gas may be located at the site in pressurized containers.

Safety precautions are necessary to assure that anesthetic gases are not transmitted in the oxygen delivery line and vice versa. Prior art safety precautions generally utilized one or a combination of several techniques to provide this assurance.

Standard medical practice incorporates a color coding system for gas containers and delivery lines for anesthetic gas or gases used in association with anesthetic gases. Oxygen tanks or like containers and delivery lines for oxygen are color coded green. Anesthetic gas tanks or like containers and delivery lines are also color coded, for example, nitrous oxide gas containers and ancillary delivery equipment are color coded blue. At the situs of the delivery of the anesthetic gases and oxygen-containing gas, e.g., an operating room there are generally three techniques or safety precautions which are used to assure the delivery of the proper gas component in the designated line. The most common of the techniques is the provision of interlocking connectors at the outlet station for the gases being delivered. The connectors are keyed, sized, or otherwise made compatible only with the appropriate gas outlet from the delivery lines. Therefore, an oxygen gas connector would not interfit with the anesthetic gas delivery line and vice versa.

As noted earlier, generally, oxygen or oxygen-containing gas is intermixed with the anesthetic gas prior to administration to the patient. An example of a conventional intermixing device or flow meter is the ANALOR flow meter manufactured by McKesson Inc., Moncks Corner, S.C. which operates generally on the principle of modification of the presence of the gas being transmitted for intermixing to control the requisite volume flow of the said gas. In the use of nitrous oxide as an anesthetising gas, the normal range in volume percent of the intermixed nitrous oxide and pure oxygen gas is 65-70 volume percent nitrous oxide and 35-30 volume percent oxygen. However, this range is subject to significant modification both for nitrous oxide and other conventional anesthetising gases, such as HALOTHANE, a tradename of Ayerst Laboratories, Rockville, Md. and methoxyfurane.

An additional precautionary measure which may be utilized to prevent an imbalance in the regulated flow of the anesthetizing gas mixture is the affixation of a pressure monitoring device on the oxygen or oxygen-containing gas line prior to the gas intermixing device. As the gas pressure in the oxygen line decreases, and therefore, the flow or volume of gas being delivered decreases, the pressure monitoring device will shut down the flow of the anesthetic gas.

The prior art discloses a third precautionary measure—an oxygen analyzer, which in essence measures the percentage of oxygen in the intermixed anesthetic gas subsequent to the intermixing of the anesthetic gas and the oxygen or oxygen containing gases. These oxygen monitoring systems generally utilize the polarographic method for monitoring the percentage of oxygen gas present in the anesthetic gas mixture. The use of the polarographic technique for oxygen monitoring is disadvantageous due to the time consuming and exacting process of maintaining the electrode system required in the polarographic testing procedure, which may require membrane replacement on a weekly basis.

As is evident from this synopsis of prior art cautionary techniques, there is no present method to assure that oxygen or oxygen-containing gas is being delivered by the oxygen delivery line prior to intermixing with the anesthetic gas. If, for example, there was a coupling error in the central storage system or a mislabeling problem with the gas storage tanks, there is no present technique to assure that only oxygen or oxygen-containing gas is being delivered by the oxygen delivery system. The presence of anesthetic gases in the oxygen delivery system has caused a significant number of patient deaths due to the administration of more anesthetic gas than the anesthetist would believe was being administered.

SUMMARY OF THE INVENTION

Accordingly, it is the object of the present invention to provide a relatively inexpensive, efficient and dependable method and apparatus for detecting the presence of anesthetic gases in oxygen delivery lines prior to mixing of the anesthetic gas and oxygen or oxygen-containing gases.

In the invention, there is provided a sensor to develop a first signal when the presence of anesthetic gas in the oxygen delivery line is detected. The first signal is used to generate an output signal which is transmitted to an audio and/or visual warning device or means which will shut off the incoming oxygen gas stream.

A further object of the invention is the utilization of a monitoring means which may be controlled to specifically monitor the presence of anesthetic gas in the oxygen line by spectroscopic analysis, for example, infrared spectroscopic absorption in association with a sensor to detect the presence of anesthetic gas in the oxygen delivery line. Further objects, advantages, and features of the invention will be apparent in the arrangement and construction of the constituent parts in detail as set forth in the following specification taken together with the accompanying drawing.

DESCRIPTION OF THE DRAWING

In the drawing,

FIG. 1 is a schematic presentation of the apparatus of the invention.

DETAILED DESCRIPTION OF THE PREFERRED EMBODIMENT

The invention can be described with reference to the preferred embodiment illustrated schematically in the drawing. There is shown a portion of the oxygen or oxygen-containing gas delivery system prior to mixing with the anesthetic gas for subsequent administration to the patient.

All or a portion of the oxygen or oxygen-containing gas is conducted to detection chamber or cell 4 via conduit 14. Generally, the oxygen or oxygen-containing gas is under a moderate pressure in the range of about 30 to 50 psi. As will be appreciated, the detection chamber must be constructed to withstand the pressure under which the oxygen or oxygen-containing gas is transmitted. The oxygen or oxygen-containing gas exits detection chamber 4 by conduit 18 for direct transmission to the subsequent mixing apparatus (not shown).

A light source, for example, an infra-red light source 2, transmits infra-red energy through the detection chamber 4, which chamber has infra-red transparent windows 5 and 7 to allow transmission of the infra-red energy through the chamber 4 and the gas or infra-red energy through the chamber 4 and the gas or gases flowing through the chamber 4. The infra-red energy may be chopped using a convention chopper to provide a pulsating signal response to allow generation of a square wave by the detection device to facilitate amplification of the detection response. The infra-red energy, after transmission through the chamber 4, impacts infra-red sensor 6. As will be appreciated conventional optical focusing means (not shown) may be employed to focus the infra-red energy on the sensor 6.

Under infra-red spectroscopic principles, the presence of particular molecules in the gas flow stream will cause absorbance of infra-red energy of particularized wavelength. The sensor 6 can determine the absorbance at these wavelengths and thereby detect the presence of anesthetic gases, e.g., nitrous oxide in the oxygen or oxygen containing gas stream. In the preferred embodiment a monochrometer, or wavelength filter may be utilized at any convenient position between the infra-red source 2 and the sensor 6 to filter or otherwise particularize the infra-red wavelengths being transmitted to the sensor 6. For example, if the presence of nitrous oxide in the oxygen or oxygen-containing gas stream is being monitored, the monochrometer may be set to filter all wavelengths with the exception of infra-red energy wavelength of about 7.6 to about 8.0 microns, preferably 7.7 to 7.9 and most preferable about 7.8 microns. The presence of nitrous oxide in the gas stream will absorb all or a portion of this infra-red energy wavelength. The decreased intensity or absence of this wavelength will be detected by the sensor 6, thereby generating a signal which may be amplified by conventional means utilizing amplifier 8 and transmitted to the signal processing and control logic indicated at 10. As will be appreciated the wavelength transmission through the monochrometer may be varied to appropriate wavelength for other anesthetic gases used in conventional medical practice, e.g., HALOTHANE having a particularized infra-red absorbance wavelength of 3.4–3.5 microns, preferable 3.5 microns, or other anesthetic gases having similar chemical structures specifically halogenated hydrocarbons and methoxyflurane having a particularized infra-red absorbance wavelength of about 8.7–9.4 microns, more preferably about 8.8–9.1 and most preferably about 9.0 microns, and other anesthetic gases, specifically halogenated aliphatic ethers, having absorbance peaks in the above broad range defined for methoxyfurane.

The signal processing and control logic 10 will transmit a second signal to visual or audio warning indicators 12. In addition to warning indicators 12, the processing and control logic 10 may be connected to a relay operated solonoid valve 16 which is located on conduit 18. Upon receipt of the signal indicating the presence of anesthetic gas in the oxygen gas flow stream the solonoid valve 16 will be activated ceasing further transmission of the contaminated gas to the mixing apparatus (not shown) and subsequent administration to the patient. The sensitivity of the preferred embodiment for usage with nitrous oxide as the anesthetizing gas allows detection of as little as 5 volume percent of nitrous oxide in the oxygen or oxygen-containing gas stream. The sensitivity of the device is of course cost dependent upon the degree of amplification of the signal, monochrometer resolution and transparency of the cell windows. There are a significant number of infra-red spectrometers which may be adapted for utilization in the instant invention. A spectrometer which has been found to be readily adaptable to the instant invention is the MIRAN-1A General Purpose Infra-red Analyzer manufactured by Foxboro Analytical, a division of The Foxboro Company.

The method and apparatus of the invention monitors the presence of anesthetic gas in the oxygen or oxygen-containing delivery lines continuously by a nondestructive method and therefore produces no by-products which could be injurious to the patient. Additionally, while a purge stream of the gas stream may be analyzed, in the preferred embodiment, monitoring of the entire oxygen or oxygen-containing gas stream, being subsequently transmitted to the patient, is conducted.

While there has been shown and described what is considered to be preferred embodiment of the present invention, it will be obvious to those skilled in the art that various changes and modifications may be made therein without departing from the invention as defined in the appended claims.

I claim:

1. An apparatus for use with a system for administration of anesthetics comprising predominantly a mixture of anesthetic gas and oxygen-containing gases, said apparatus comprising a sensor for detecting the presence of anesthetic gas in an oxygen or oxygen-containing gas delivery line prior to mixing said oxygen or oxygen-containing gas with the said anesthetic gas; said sensor being capable of developing a signal upon detection of said anesthetic gas in said oxygen or oxygen-containing gas delivery line, and means responsive to the signal developed for indicating the presence of said anesthetic gas in said oxygen or oxygen-containing gas delivery line which activates a warning or shuts off the oxygen or oxygen-containing gas delivery line.

2. An apparatus as recited in claim 1, wherein said sensor is an infra-red spectrometer comprising a detection cell through which all, or a portion of the gases, in the oxygen or oxygen-containing gas delivery line pass, an infra-red energy source capable of directing infra-red energy into the detection cell, and detector means to detect the presence of anesthetic gas in the detection cell due to infra-red absorption of a particular portion of the infra-red energy by the anesthetic gas molecules present in the cell.

3. An apparatus as recited in claim 2 further including means to filter infra-red energy transmitted by the infra-red source such that the infra-red energy has a wavelength which will be absorbed by the said anesthetic gas.

4. An apparatus of claim 2 or 3, wherein the signal developed by the detector means is transmitted to a visual or audio warning device to indicate the presence of anesthetic gas in the oxygen or oxygen-containing gas delivery line.

5. An apparatus of claim 2 or 3, wherein the signal developed by the detector means is transmitted to shut off device located in the oxygen or oxygen-containing gas delivery line which device is actuated to shut off the incoming oxygen or oxygen-containing gas stream upon detection of the presence of anesthetic gas.

6. The apparatus of claims 1, or 2 wherein the sensor detects the anesthetic gas nitrous oxide.

7. The apparatus of claim 3 wherein the transmitted infra-red energy has a wavelength of about 7.7 to 7.9 microns and preferably 7.8 microns.

8. In a method for the detection of anesthetic gas in an oxygen or oxygen-containing gas delivery line used in the administration of anesthetics, the steps for detecting the presence of anesthetic gas in said oxygen delivery line comprising:
  (a) passing all, or a portion, of the gas in said delivery line through a detector cell capable of withstanding moderate positive pressure while transmitting infra-red energy through said detector cell;
  (b) recepting said transmitted infra-red energy by an infra-red sensor capable of determining the presence of anesthetic gas in said detector cell; and,
  (c) generating a signal by said infra-red sensor when the presence of an anesthetic gas is detected.

9. In the method of claim 8, further including amplifying the signal generated by the said infra-red sensor and transmitting the said amplified signal to a visual or audio warning device.

10. In the method of claim 8 or 9, transmitting said signal to a shut off device located in the oxygen or oxygen-containing gas delivery line to shut off the incoming oxygen or oxygen-containing gas stream upon detection of the presence of anesthetic gas.

11. In the method of claim 9, transmitting infra-red energy having a wavelength of about 7.7 to 7.9 microns and preferably about 7.8 microns through said detector cell to detect the presence of nitrous oxide.

12. In the method of claim 10, transmitting infra-red energy having a wavelength of about 7.7 to 7.9 microns and preferably about 7.8 microns through said detector cell.

* * * * *